United States Patent [19]
Umezawa et al.

[11] 3,973,608
[45] Aug. 10, 1976

[54] MICROBIAL PRODUCTION OF CERTAIN ISOFLAVONES

[75] Inventors: Hamao Umezawa; Tomio Takeuchi; Hideo Chimura, all of Tokyo; Tsutomu Sawa, Ayase; Masa Hamada, Hoya, all of Japan

[73] Assignee: Zaidan Hojin Biseibutsu Kagaku Kenkyu Kai, Tokyo, Japan

[22] Filed: May 19, 1975

[21] Appl. No.: 578,709

Related U.S. Application Data

[62] Division of Ser. No. 490,839, July 23, 1974.

[30] Foreign Application Priority Data

Aug. 1, 1973  Japan.................................. 48-85884

[52] U.S. Cl............................................... 195/80 R
[51] Int. Cl.$^2$............................................. C12D 9/00
[58] Field of Search ................................... 195/80 R

[56] References Cited

OTHER PUBLICATIONS

International Journal of Systematic Bacteriology; vol. 18; p. 167; 1968.

Primary Examiner—A. Louis Monacell
Assistant Examiner—Robert J. Warden
Attorney, Agent, or Firm—Herbert W. Taylor, Jr.

[57] ABSTRACT

This invention relates to the novel compounds 3',5,7-trihydroxy-4',6-dimethoxy-isoflavone, 3',5,7-trihydroxy-4',8-dimethoxy-isoflavone and 3',7-dihydroxy-4',6,8-trimethoxy-isoflavone which are powerful inhibitors of catechol-O-methyl transferase (COMT) and to their production by fermentation of *Actinomyces roseolus*.

6 Claims, No Drawings

MICROBIAL PRODUCTION OF CERTAIN ISOFLAVONES

CROSS-REFERENCE TO RELATED APPLICATIONS

This application is a division of our prior copending application United States Ser. No. 490,839 filed July 23, 1974.

SUMMARY OF THE INVENTION

There is provided by the present invention the three compounds having the formula

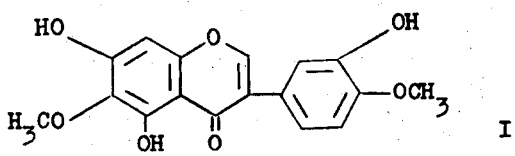

I,

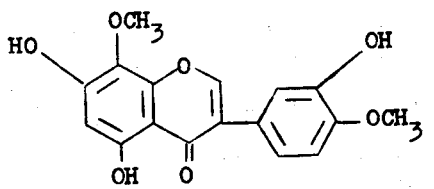

II and

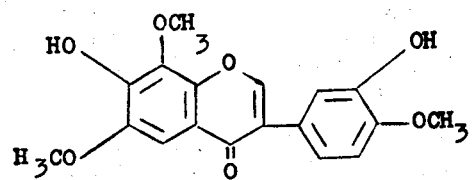

III

There is also provided by the present invention the process for the production of the compound having the formula

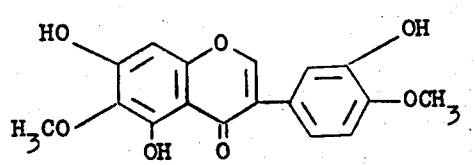

which comprises cultivating *Actinomyces roseolus* at a temperature of about 25° to 35° C. for at least 2 days under submerged aerobic conditions in an aqueous assimilable carbohydrate solution containing an assimilable nitrogenous nutrient until a substantial amount of said compound is produced in said solution and then recovering said compound and also said process which utilizes a strain of *Actinomyces roseolus* having the characteristics of strain A.T.C.C. 31047 and also said process wherein said compound is recovered from the fermentation broth by solvent extraction at an acidic pH and then purified by chromatographic adsorption and elution.

There is also provided by the present invention the process for the production of the compound having the formula

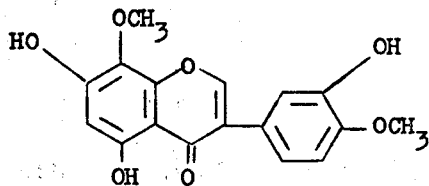

which comprises cultivating *Actinomyces roseolus* at a temperature of about 25° to 35° C. for at least 2 days under submerged aerobic conditions in an aqueous assimilably carbohydrate solution containing an assimilably nitrogenous nutrient until a substantial amount of said compound is produced in said solution and then recovering said compound and also said process which utilizes a strain of *Actinomyces roseolus* having the characteristics of strain A.T.C.C. 31047 and also said process wherein said compound is recovered from the fermentation broth by solvent extraction at an acidic pH and then purified by chromatographic adsorption and elution.

There is also provided by the present invention the process for the production of the compound having the formula

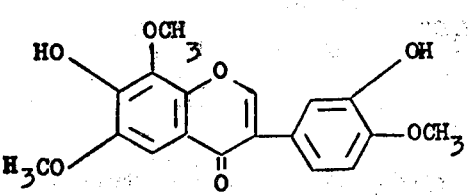

which comprises cultivating *Actinomyces roseolus* at a temperature of about 25° to 35° C. for at least two days under submerged aerobic conditions in an aqueous assimilable carbohydrate solution containing an assimilable nitrogenous nutrient until a substantial amount of said compound is produced in said solution and then recovering said compound and also said process which utilizes a strain of *Actinomyces roseolus* having the characteristics of strain A.T.C.C. 31047 and also said process wherein said compound is recovered from the fermentation broth by solvent extraction at an acidic pH and then purified by chromatographic adsorption and elution.

Finally, there is provided by the present invention a method for producing novel isoflavone compounds (I, II and III) having inhibiting actions against a catechol-O-methyl transferase and expressed by a general formual

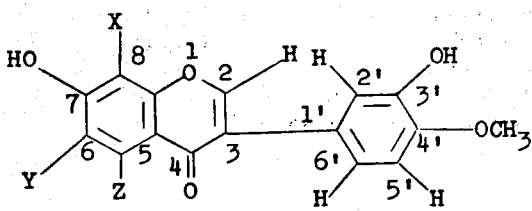

werein,
X = H, Y = OCH₃, Z = OH (Compound I)
X = OCH₃, Y = H, Z = OH (Compound II)
X = OCH₃, Y = OCH₃, Z = H (Compound III)
the method being characterized in that strain of actinomyces of a type producing said isofalvone compounds is cultured and said isoflavone compounds are collected from the thusly cultured actinomyces.

DETAILED DESCRIPTION OF THE INVENTION

This invention relates to a method for producing 3',5,7-trihydroxy-4',6-dimethoxy-isoflavone having the structure

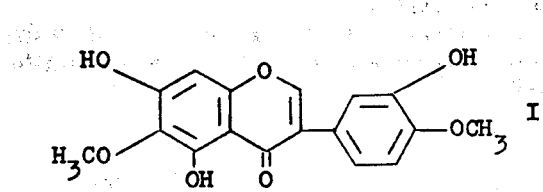

3',5,7-trihydroxy-4',8-dimethoxy-isoflavone having the structure

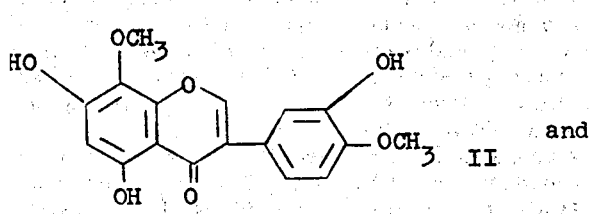

3',7-dihydroxy-4',6,8-trimethoxy-isoflavone havine the structure

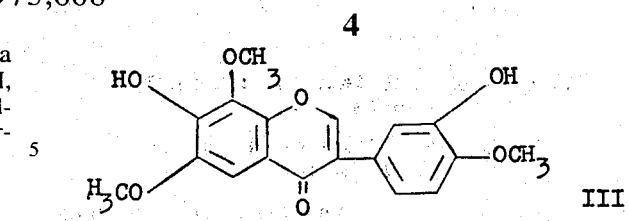

which act as powerful inhibitors of a catechol-O-methyl transferase (hereinafter referred to as COMT) and, more particularly, to a method wherein these compounds are recovered from a cultured microorganism.

In a systematic research for inhibitors against COMT which methylates the meta-position hydroxyl group in the catechol skeleton of catchol amines, the inventors discovered the presence of such inhibitors in the culture solution as well as in the body of an Actinomyces. These inhibitors were separated and purified, and then subjected to a study to determine their chemical structure which showed that they have an isoflavone skeleton. Further research also showed that they were novel compounds having chemical structures (I), (II) and (III) as shown above, and led the inventors to the method of this invention wherein these compounds were recovered from a cultured microorganism.

No report has been presented heretofore of the detection of compounds (I), (II) and (III) in either natural substances or in artifically synthesized materials. Thus these compounds have been obtained for the first time by the inventors.

It has been reported heretofore that an inhibitor against COMT delays the metabolism or rate of destruction of adrenaline, noradrenaline, etc. in the human body and, therefore, serves to prolong and promote their blood pressure elevating action. These inhibitors may also be used as curative or palliative medicines for diseases such as depression which is considered to be caused when catechol amines present in the human body are reduced in quantity. There has been much argument about etiological causes of schizophrenia. One hypothesis says that the schizophrenia is caused by the production of abnormally methylated bioamines (methylated catechol amines and serotonin) within the brain. Especially, hallucination of schizophrenia is said to be caused by abnormally methylated catechol amines (Ref. "Amines and Schizophrenia" by H. E. Himwich, S. S. Kety and J. R. Smythies, 1967, Pergamon Press, Oxford). The inhibitors of COMT may therefore be used as curative medicines for schizophrenia and for the associated hallucination. On the other hand, the anti-hemochlasis of isoflavones has been reported by Murata and Ikehata ("Agr. Biol. Chem.," Vol. 32, No. 6, 1968, pp. 740–746) and the cholesterol deposition preventing action of isoflavones has been reported by G. W. Moersch, D. F. Morrow and W. A. Neuklis ("J. Med. Chem." 10(2), 1967, pp. 154–158). By use of the method proposed by V. F. Davis and J. Awapara for measuring the activity of DOPA decarboxylase, the inventors measured the degree of inhibition of the compounds (I), (II) and (III) against the DOPA decarboxylase and found that the compounds (I) and (II) had a powerful inhibiting action, while the compound (III) exhibited no inhibiting action. The inventors also found that the compounds (I), (II) and (III), when applied to spontaneously hypertensive rats lowered the blood pressure of the rats. It will therefore be possible to use the compounds (I), (II) and (III) as curative medicines for diseases such as hypertension and arteriosclerosis and also as economizers in combination with DOPA for treating Parkinson's disease. It was also found that the compounds (I) and (II) inhibit histidine decarboxylase. This means that there is a possibility to use the compounds (I) and (II) as curative medicines for inflammation and allergy in man.

Heretofore, these isoflavones were unknown. The inventors established a method for efficiently obtaining said isoflavones (I), (II) and (III). According to the method *Actinomyces roseolus* or International Standard Strain ISP 5174 of actinomyces (Ref. "International Journal of Systematic Bacteriology" Vol. 18, 1968, p. 167, by E. B. Shirling et al.; "Zur Klassifizierung der Actinomyceten", 1958, p. 28, by G. F. Gause, Veb Gustav Fischer Verlag, Jena) is cultured and said isoflavones are collected from the cultured *Actinomyces roseolus*

The Research Institute for Microbial Industrial Technology belonging to the Japanese Agency of Industrial Science and Technology has taken custody of a culture of said strain as their Microorganism Deposition No. 1,906 and another culture has been deposited in the American Type Culture Collection, Washington, D. C. under their accession number A.T.C.C. 31047.

More specifically, according to this invention the compounds (I), (II) and (III) can be obtained from the cultured microorganism which can be prepared by culturing the strain thereof in an ordinary well-known manner. For example, *Actinomyces roseolus* which is capable of producing the compounds (I), (II) and (III) may first be cultured in a known type culture medium such as glycerin-asparagine-agar or yeast malt-agar culture medium and then the hypha thusly grown in the agar culture medium may be inoculated directly on a production culture medium. Alternatively, the fungus body grown in a liquid culture medium may be inoculated on a production culture medium. *Actinomyces roseolus* grows in the temperature range of 25° to 35° C., but for the purpose of producing the intended compounds it should preferably be cultured in the range of 27°–30° C.

When producing the compounds (I), (II) and (III) by culturing *Actinomyces roseolus*, any nutrients usually employed in culturing microorganisms such as molds, imperfect fungi, actinomyces, bacteria, etc. may conveniently be used. For example, glucose, maltose, lactose, saccharose, glycerin, dextrin, starch, soybean oil, molasses, etc. can be used as carbon sources. We prepared a basic culture medium which contained 2.0% of soybean cake, 0.5% of yeast extract, 0.25% of NaCl, 0.35% of $CaCO_3$, 0.0005% of $CuSO_4.5H_2O$, 0.0005% of $MnCl_2.4H_2O$ and 0.005% of $ZnSO_4.7H_2O$. To this basic culture medium were added various carbon sources to the concentrations as defined in the following Table to prepare thereby various types of culture media. A plurality of 500 cc. Sakaguchi's flasks were prepared and into each of these flasks was introduced 125 cc of each of these culture media, which was then sterilized for 20 minutes at 120° C. under pressure. On the thusly prepared culture media was inoculated a platinum loop of hypha which had been cultured separately for 14 days at 27° C. on a glycerin-asparagine-agar slant culture medium. The thusly inoculated hypha was cultured at 27° C. while shaking the media. Listed in the following Table are inhibition ratios against COMT measured 5 days after starting cultivation.

| Type and concentration of carbon source | pH | Dilution | Inhibition ratio against COMT |
|---|---|---|---|
| glycerin, 2% | 8.0 | X 2 | 28% |
| glucose, 2% | 7.5 | X 2 | 33% |
| lactose, 2% | 7.5 | X 2 | 20% |
| dextrin, 2% | 7.2 | X 2 | 30% |
| starch, 2% | 7.0 | X 2 | 30% |
| maltose, 2% | 7.2 | X 2 | 25% |
| glucose, 1% starch, 2% | 7.2 | X 2 | 58% |
| glucose, 1% soybean oil, 0.5% | 7.2 | X 2 | 30% |
| glucose, 1% saccharose, 1% | 7.5 | X 2 | 35% |
| glucose, 1% molasses, 1% | 7.8 | X 2 | 35% |

It will be seen from the Table that the listed carbon sources are all useful for producing the intended compounds but glucose and starch are preferred.

It was also found that nitrogen sources commonly employed in growing microorganisms such as actinomyces, molds, imperfect fungi, bacteria, etc. can equally be used in producing the compounds (I), (II) and (III). They are, for example, peptone, meat extract, yeast extract, soybean flour, soybean cake, corn steep liquor, Casamino acid, cottonseed flour, etc. In a similar manner to the above-described tests, to culture media containing 1% of glucose, 2% of starch, 0.25% of NaCl, 0.35% of $CaCO_3$, 0.0005% of $CuSO_4.5H_2O$, 0.0005% of $MnCl_2.4H_2O$ and 0.005% of $ZnSO_4.7H_2O$ were added various nitrogen sources as listed in the following Table. After sterilizing the thusly prepared culture media, the hypha which had been grown in a separate agar slant culture medium was inoculated and cultured for 5 days. The resulting inhibition ratios against COMT were as follows:

| Type and Concentration of nitrogen source | pH | Dilution | Inhibition ratio against COMT |
|---|---|---|---|
| meat extract, 0.75 peptone, 0.75% | 7.8 | X 2 | 18.0% |
| soybean cake, 2.0% yeast extract, 0.5% | 7.5 | X 2 | 65.0% |
| soybean flour, 2.0% | 7.5 | X 2 | 48.0% |
| soybean flour, 2.0% | 7.8 | X 2 | 45.0% |
| soybean cake, 2.0% Casamino acid, 0.5% | 7.2 | X 2 | 60.0% |
| soybean cake, 2.0% corn steep liquor, 0.5% | 7.8 | X 2 | 58.0% |
| cottonseed flour, 2.0% | 7.8 | X 2 | 48.0% |
| cottonseed flour, 2.0% yeast extract, 0.5% | 7.5 | X 2 | 51.0% |
| cottonseed flour, 2.0% Casamino acid, 0.5% | 7.8 | X 2 | 50.0% |
| cottonseed flour, 2.0% corn steep liquor, 0.5% | 7.8 | X 2 | 50.0% |

As will be seen from the Table, the listed nitrogen sources are all effective but soybean cake and yeast extract are preferred.

A very small quantity of inorganic salts, metallic salts and/or heavy metallic salts may be added. When it is required to defoam the culture medium during sterilization and/or cultivation, antifoaming agents such as silicone resin, soybean oil, etc. may also be added.

According to this invention, the compounds (I), (II) and (III) are produced by culturing *Actinomyces roseolus* under aerobic conditions, and for this purpose the aerated agitation tank culture method for use in producing antibiotics such as penicillin can be used without any substantial modification. It will be apparent to those skilled in the art that the concentrations of compounds (I), (II) and (III) in the culture liquid vary depending on the above-mentioned various conditions. It seems therefore to be an easy task for those skilled in the art to produce only a single intended compound in an efficient manner. It should be noted that all these possible modifications are comprehended within the scope of this invention.

The compounds (I), (II) and (III) can be determined by measuring inhibition of COMT. The activity of COMT is measured in accordance with the method reported by B. Nikodejevic et al. (Ref. "The Journal of Pharmacology and Experimental Therapeutics", Vol. 174, pp. 83-93, by B. Nikodejevic et al., 1970). 0.5 cc total volume of reaction liquid is prepared from 0.125 cc of water, 0.05 cc of 0.1 mole phosphate buffer solution (pH 8.0), 0.1 cc of 0.1 mole magnesium chloride solution, 0.05 cc. of 0.05 mole adrenaline solution, 0.075 cc of 0.5 millimole tritium-8-adenosyl methionine aqueous solution (2.2 × $10^5$ cpm), 0.05 cc of sample solution and 0.05 cc of enzyme solution. These solutions are mixed together at 0° C. and, after reacting for 20 minutes at 37° C., 1 cc of 0.5 mole boric acid buffer solution (pH 10.0) is added to stop the reaction. Then, tritium metanephrine ($^3$H-metanephrine) wherein the meta-hydroxyl group has been methylated is extracted with a solvent mixture such as toluene-isoamyl alcohol (3:2). A quantity of solvent portion is then sampled and its radioactivity is measured by use of a liquid scintillation counter. The thusly obtained measurement of radioactivity tells the quantity of formed methanephrine, which in turn permits one to determine the inhibition.

The compounds (I), (II) and (III) also exhibit an inhibiting action against histidine decarboxylase. This inhibition is measured in the following manner:

The reaction liquid is prepared from 2.5 × $10^{-4}$ mole of L-histidine-2-$^{14}$C (1.0 × $10^5$ cpm), 3.7 × $10^{-5}$ mole of pyridoxal phosphate, 0.1 cc of histidine decarboxylase (protein content, 1 mg/cc), 0.1 cc of 0.67 mole phosphate buffer solution (pH 6.8) and sample solution. To this mixture there is added distilled water until 1 cc total volume of reaction liquid is obtained. The thusly prepared reaction liquid is then allowed to react for 2 hours at 37° C. and the formed histamine-2-$^{14}$C is adsorbed on ammonia type "Amberlite CG-50". After washing the Amberlite CG-50 with water, the adsorbed histamine is eluted with 1 N aqueous ammonia and a quantity of elute is sampled to measure its radioactivity by use of a liquid scintillation counter. The thusly measured radioactivity tells the quantity of formed histamine, so that the inhibition against histidine decarboxylase can be determined.

Now the extractive purification of the compounds (I), (II) and (III) will be described. It is found that these compounds are soluble in alkaline water, methanol, ethanol and acetone and slightly soluble in butanol, ethyl acetate and butyl acetate. These compounds are extracted from the culture filtrate under acidic conditions with butanol, butyl acetate, etc. or also from the fungus solid body (mycelium) with methanol, acetone, etc. The filtrate from the mycelial extract is concentrated by distillation under diminished pressure and the concentrated liquid, after having been adjusted to be acidic, is subjected to an extraction operation with butyl acetate or butanol. The thusly extracted liquid is mixed with the solution of butyl acetate or butanol separately extracted from the culture liquid, and then concentrated to dryness under diminished pressure.

The extracted solid is then triturated with petroleum ether or n-hexane leaving the purified compounds as the solid, insoluble portion. When the insoluble portion is further extracted with acetone, the active portion is transferred into the acetone solvent and the solid residues can be removed as impurities. The acetone extract liquor is concentrated to dryness under diminished pressure and chromatographed through a silica gel column and then eluted with benzene:acetone (10:1) mixture until it is separated into three fractions having high activities. The active materials contained in each active fraction are then purified through "Sephadex LH-20" column chromatography, alumina column chromatography and, if necessary, silica gel column chromatography. Thus, the compounds (I), (II) and (III) are isolated in crystalline form from the first active fraction, second active fraction and third active fraction, respectively.

These compounds have physico-chemical properties as listed in Table 1. As a result of study of the chemical structure thereof, the inventors determined that the first compound (I) was 3',5,7-trihydroxy-4',6-dimethoxy-isoflavone, the second compound (II) was 3',5,7-trihydroxy-4',8-dimethoxy-isoflavone and the third compound (III) was 3',7-dihydroxy-4',6,8-trimethoxy-isoflavone.

TABLE 1 (1)

| Physico-chemical property | Compound (I) |
|---|---|
| State (melting point) | light yellow needle (176°C.) |
| Elementary analysis value (%) | C: 61.92; H: 4.31; 0: 33.28 |
| Mass spectrum | 330 |
| Molecular formula (molecular weight) and theoretical value | $C_{17}H_{14}O_7$ (330.28) |
|  | C: 61.82; H: 4.27; 0: 33.91 |
| Ferric chloride reaction | ⊕ blue-violet |
| Gibbs' reaction | violet |
| Number of -OCH$_3$ (from NMR) | 2 |
| Introduction number of acetyl group (from NMR) | 3 |
| Ultraviolet absorption ($\lambda$ max) |  |
| 1. ethanol | 1) 269.0 nm (log $\epsilon$ :4.305) 295nm(s) |
| 2. ethanol (aluminium chloride) | 2) 284.0 nm (log $\epsilon$ :4.301).- |
| 3. NaOAc saturated ethanol | 3) 278.0 nm (log $\epsilon$ :4.307) 340nm(s) |
| Infrared absorption spectrum (cm$^{-1}$) | 3500 1655 1630 1585 1520 1478 1380 1300 1265 1200 1175 1130 1070 1028 1000 |

TABLE 1 (1)-continued

| Physico-chemical property | Compound (I) | |
|---|---|---|
| | 970 905 875 830 815 | |
| | 755 732 675 | |
| NMR (DMSO-$d_6$) | 13.20 (OH) | : S |
| 100 MHz (ppm) | 10.74 (OH) | : M |
| | 9.05 (OH) | : M |
| | 8.33 (H) | : S |
| | 7.05 (H) | ] *aromatic proton |
| | 6.97 (2H) | |
| | 6.52 (H) | : S. aromatic proton |
| | 4.78 (3H) | : S $OCH_3$ |
| | 4.82 (3H) | : S $OCH_3$ |
| Thin-layer chromatography (silica gel) | $R_f$ | |
| benzene: acetone (5:1) | 0.30 | |
| chloroform: methanol (40:1) | 0.50 | |
| benzene: ethyl acetate (1:1) | 0.65 | |

TABLE 1 (2)

| Physico-chemical property | Compound (II) | |
|---|---|---|
| State (melting point) | yellow needle (203° C.) | |
| Elementary analysis value (%) | C: 61.63; H: 4.50; O: 34.31 | |
| Mass spectrum | 330 | |
| Molecular formula (molecular weight) and theoretical value | $C_{17}H_{14}O_7$ (330.28) C: 61.82; H: 4.27; O: 33.91 | |
| Ferric chloride reaction | ⊕ blue-violet | |
| Gibbs' reaction | yellow-violet | |
| Number of -$OCH_3$ (from NMR) | 2 | |
| Introduction number of acetyl group (from NMR) | 3 | |
| Ultraviolet absorption ($\lambda$ max) | | |
| 1. ethanol | 1) 269.0 nm (log $\epsilon$ : 4.312) 295 nm(s) | |
| 2. ethanol (aluminium chloride) | 2) 285.0 nm (log $\epsilon$ : 4.320). | |
| 3. NaOAc saturated ethanol | 3) 279.0 nm (log $\epsilon$ : 4.310) | |
| Infrared absorption spectrum ($cm^{-1}$) | 3450 1655 1620 1580 1515 1435 1370 1310 1270 1195 1170 1130 1065 1030 994 945 905 880 825 810 755 725 675 | |
| NMR (DMSO-$d_6$) | 12.63 (OH) | : S |
| 100 MHz (ppm) | 10.75 (OH) | : M |
| | 9.04 (OH) | : M |
| | 8.40 (H) | : S |
| | 7.06 (H) | ] aromatic proton |
| | 6.97 (2H) | |
| | 6.33 (H) | : S. aromatic proton |
| | 3.78 (3H) | : S $OCH_3$ |
| | 3.81 (3H) | : S $OCH_3$ |
| Thin-layer chromatography (silica gel) | $R_f$ | |
| benzene: acetone (5:1) | 0.25 | |
| chloroform: methanol (40:1) | 0.31 | |
| benzene: ethyl acetate (1:1) | 0.60 | |

TABLE 1 (3)

| Physico-chemical property | Compound (III) |
|---|---|
| State (melting point) | colorless needle (215°C.) |
| Elementary analysis value (%) | C: 62.86; H: 4.79; O: 32.35 |
| Mass spectrum | 344 |
| Molecular formula (molecular weight) and theoretical value | $C_{18}H_{16}O_7$ (344.31) C: 62.97; H: 4.68; O: 32.53 |
| Ferric chloride reaction | ⊕ |
| Gibbs' reaction | blue |
| Number of -$OCH_3$ (from NMR) | 3 |
| Introduction number of acetyl group (from NMR) | 2 |
| Ultraviolet absorption ($\lambda$ max) | |
| 1. ethanol | 1) 268.0 nm (log $\epsilon$ :4.314) 295 nm(s) |
| 2. ethanol (aluminium chloride) | 2) 268.0 nm (log $\epsilon$ :4.315) 295 nm(s) |
| 3. NaOAc saturated ethanol | 3) 285 nm (log $\epsilon$ :4.310) |
| Infrared absorption spectrum ($cm^{-1}$) | 3500 1650(S) 1615 1580 1515 1475 1355 1310 1300 1270 1210 1195 1130 1100 1050 |

TABLE 1 (3)-continued

| Physico-chemical property | Compound (III) | |
|---|---|---|
| NMR (DMSO-$d_6$) 100 MHz (ppm) | 1025 1000  985 960 900 | |
| | 865 805  785 760 710 | |
| | 10.00 (OH) | : M |
| | 9.00 (OH) | : M |
| | 8.39 (H) | : S |
| | 7.07 (H+H) | ⎤ aromatic proton |
| | 6.98 (2H) | ⎦ |
| | 3.90 (3H) | : S OCH$_3$ |
| | 3.83 (3H) | : S OCH$_3$ |
| | 3.81 (3H) | : S OCH$_3$ |
| Thin-layer chromatography (silica gel) | | $R_f$ |
| benzene: acetone (5:1) | | 0.19 |
| chloroform: methanol (40:1) | | 0.31 |
| benzene: ethyl acetate (1:1) | | 0.50 |

Now the compounds (I), (II) and (III) will be described with respect to their biological properties. It was found that the compounds exhibited no toxicity at a dosage of 200 mg./kg. when they were dissolved in a 25% aqueous solution of dimethyl sulfoxide and administered into the abdominal cavity of rats.

By use of the previously mentioned method, the concentrations of the compounds at which they inhibited the activity of COMT by 50% were measured: compound (I), 0.5 γ/cc (1.515 × 10$^{-6}$ mole); compound (II), 5.0 γ/cc (1.515 × 10$^{-5}$ mole); compound (III), 0.2 γ/cc (5.80 × 10$^{-7}$ mole). When measured by use of the methods as disclosed by the inventors in the parenthesized Journal, these compounds showed no inhibiting action at a concentration of 100 γ/cc against tyrosine hydroxylase ("J. Antibiotics", 21, 350, 1968) and dopamin-β-hydroxylase (J. Antibiotics, 21, 354, 1968). Also, inhibition against the DOPA decarboxylase was measured in accordance with the already mentioned method. The compounds (I) and (II) showed 50% inhibition at a concentration of 12.5 γ/cc (3.79 × 10$^{-5}$ mole) and 5.0 γ/cc (1.515 × 10$^{-5}$ mole), respectively; whereas the compound (III) showed no inhibition even at a concentration as high as 100 γ/cc. The inhibition against histidine decarboxylase was measured by the already mentioned method to find that the compounds (I) and (II) showed 50% inhibition ratio at 6.0 γ/cc (1.8 × 10$^{-5}$ mole) and 1.5 γ/cc (4.5 × 10$^{-6}$ mole), respectively; whereas the compound (III) showed an inhibition ratio of as low as about 31.9% at a concentration of 100 γ/cc. It will be noted from the foregoing results the the compound (III) is an extremely unique compound presenting an inhibiting action only against COMT and not against the other enzymes.

It was also found that the compounds (I), (II) and (III) showed no inhibiting action at a concentration of 100 γ/cc against the growth of bacteria and fungi. The inventors also examined the blood pressure lowering action of the compounds (I), (II) and (III) by administering them in the abdominal cavity of spontaneously hypertensive rats. When administered at a dosage of 50 mg./kg., the compound (I) exhibited a blood pressure lowering action of 20.8% after 1 hour, 16.4% after 3 hours, 35.0% after 6 hours and 3.9% after 24 hours; whereas when administered at a dosage of 12.5 mg./kg., 13.6% after 1 hour, 10.7% after 3 hours, 5.8% after 6 hours and 7.8% after 24 hours. When administered at a concentration of 50 mg./kg., the compound (II) exhibited a blood pressure lowering action of 22.3% after 1 hours, 35.9% after 3 hours, 15.3% after 6 hours, 23.9% after 24 hours and 16.3% after 48 hours; whereas when administered at a dosage of 12.5 mg./kg., 10.4% after 1 hours, 34.4% after 3 hours, 32.8% after 6 hours, 18.0% after 24 hours and 18.0% after 48 hours; when administered at a dosage of 3.1 mg./kg., 21.0% after 1 hour, 26.3% after 3 hours, 28.0% after 6 hours, 22.0% after 24 hours and 13.4% after 48 hours. When the compound (III) was administered at a dosage of 50 mg./kg., it exhibited a blood pressure lowering action of 11.9% after 1 hour, 13.0% after 3 hours, 17.3% after 6 hours, 7.0% after 24 hours and 3.0% after 48 hours.

Now the method for producing the novel isoflavone compounds (I), (II) and (III) will be described hereinunder with reference to several preferred embodiments. Having disclosed hereinbefore that the compounds (I), (II) and (III) can be obtained from certain microorganisms, many alterations and modifications of the method disclosed herein will be apparent to those skilled in the art. As is seen from inventors' systematic study about the enzyme inhibiting substances, the microorganisms which can produce enzyme inhibiting substances are not limited only to the specific type of actinomyces as mentioned hereinbefore. It is therefore an easy task for those skilled in the art to produce these compounds by use of other types of actinomyces than specified previously. It should be noted that these and other modifications are all comprehended within the scope of this invention. The following examples are set forth only for illustrative purposes and not for limiting this invention.

"Sephadex LH-20" is a lyophilic insoluble molecular-sieve chromatographic medium made by cross-linking dextran and marketed by Pharmacia, Uppsala, Sweden.

"Amberlite CG-50" is chromatographic grade "Amberlite IRC-50" which is a weak cation-exchange resin of the carboxylic acid type having a polystyrene base; thus resin Amberlite IRC-50 is a commercially available cation exchange resin of the carboxylic type (U.S. Pat. No. 2,340,711) which is a copolymer of methacrylic acid and divinylbenzene. It is available from Rohm and Haas, Washington Square, Philadelphia, Pa., U.S.A.

The compounds of this invention are usually administered after being compounded and formulated into pharmaceutical preparations in unit dosage form for oral or parenteral administration with organic or inorganic solid materials or liquids which are pharmaceutically acceptable carriers. Some examples of the carriers which are used are gelatin capsules, sugars, cellulose derivatives such as carboxymethylcellulose, gelatin, talc, magnesium stearate, vegetable oil such as peanut oil, etc., liquid petroleum, glycerin, sorbitol, ethanol, agar, elixirs, syrups and water including sterile water. The compositions take the form of tablets, powders, granules, capsules, suspensions, solutions and the like.

The compounds of this invention are administered orally or parenterally to mammals. A dosage range of about 0.05 to 500 milligrams per kilogram of body weight per day is convenient which may be administered in divided dosage, e.g., two, three or four times a day. Administration of the compounds is conveniently begun at the minimal effective dose (MED) of the particular compound in the particular species of mammal. However, in general, the particular dosage most suitable for a particular application, as might be expected, will vary with the age, weight and general health of the mammal under treatment and the degree of effect required. After taking into consideration these factors and any other factors to be considered, one skilled in the art of treating diseases of mammals can readily determine the appropriate dosage.

In the treatment of man, the compounds of this invention are administered orally or parenterally in accordance with conventional procedures in an amount of from about 0.05 to 500 mg./kg./day and preferably about 5 to 20 mg./kg./day in divided dosage, e.g. three to four times a day. They are administered in dosage units containing, for example, 5, 25, 125, 250 or 500 mg. of active ingredient with suitable physiologically acceptable carriers or excepients.

Due to their enzyme inhibiting activity, the compounds of this invention are useful as catechol-O-methyl transferase inhibiting agents in human and veterinary medicine. These compounds are useful in the treatment of various diseases and disorders in in which destruction of adrenalin or noradrenalin or presence of methylated catechol amine plays a role. Such diseases and disorders include but are not limited to hypertension, depression, schizophrenia and associated hallucinations, and arteriosclerosis.

Compounds I and II of this invention are useful as histidien decarboxylase inhibiting agents in human and veterinary medicine. There are therefore useful in the treatment of diseases and disorders in which excess histamine plays a role and causes inflammation or allergy such as asthma, rashes, rheumatism and arthritis.

DESCRIPTION OF THE PREFERRED EMBODIMENTS

EXAMPLE 1

To produce the compounds (I), (II) and (III) *Actinomyces roseolus* (A.T.C.C. 31047) was grown for 14 days on a glycerin-asparagine-agar slant culture medium. A production culture medium was prepared from 2% of soybean cake, 1% of glucose, 2% of starch, 0.25% of NaCl, 0.35% of $CaCO_3$, 0.0005% of $CuSo_4.5H_2O$, 0.0005% of $MnCl_2.4H_2O$ and 0.005% of $ZnSO_4.7H_2O$ and, before sterilization, adjusted to pH 7.4. This medium was then pipetted into 500 cc Sakaguchi's flasks, 120 cc each time, and sterilized at 120°C. for 20 minutes. On each of these culture media was inoculated one platinum loop quantity of hypha of said cultured *Actinomyces roseolus*. The thusly inoculated hypha was cultured at 27° C. for 5 days in a reciprocal shaker oscillating at 130 cycles/min. The measurement of pH was 7.0 after sterilization, 6.2 after (10:1) 2 days, 6.4 after 3 days, 6.8 after 4 days and 7.2 after 5 days. The analysis of reducing sugar by use of Bertrand's method showed that the residual sugar content in the medium varied as the culture process proceeded: 2.85% after 2 days, 1.00% after 3 days, 0.55% after 4 days and 0.25% after 5 days. 5000 cc culture solution was filtered to obtain 4000 cc filtrate which, when diluted to a half-concentration, showed 64% inhibition against COMT. Said 4000 cc filtrate was adjusted with 2 N HCl to pH 2.00 and extracted with 4000 cc butyl acetate (yield, 80%). When the extraction liquor was concentrated to dryness at 40°C. under diminished pressure, 18.5 g. of reddish brown syrupy material was obtained. When this material was treated with 1000 cc of petroleum ether, 7.5 g. of petroleum ether-insoluble portion was obtained. At a concentration of 250 $\gamma$/cc this portion showed 50% inhibition against COMT; whereas the petroleum ether-soluble portion scarcely showed any inhibition against COMT. The obtained petroleum ether-insoluble portion was dissolved in 100 cc of acetone and, after removing the insoluble portion, 30 g. of silica gel (manufactured by Mallinckrodt, AR-100-200 mesh) was added to the acetone solution, which was then concentrated to dryness under diminished pressure. By use of a 5 × 80 cm column packed with 300 g. of said Mallinckrodt silica gel (which had been gelled with benzene:acetone (101:1) solvent system) charged with the dried sample at the top end thereof and when said dried material was chromatographed with said solvent system, the active portion was separated into three fractions. When 750 cc of first fraction was concentrated to dryness, 58.0 mg. of 3′,5,7-trihydroxy-4′,6-dimethoxy-isoflavone (I) as a light yellow powder was obtained; from 1000 cc of second fraction, 24.0 mg. of 3′,5,7-trihydroxy-4′,8-dimethoxy-isoflavone (II) as a yellow powder was obtained and from 1500 cc of third fraction, 12.5 mg. of 3′,7-dihydroxy-4′,6,8-trimethoxy-isoflavone (III) as a brown powder was obtained. It was found that these powders showed 50% inhibition against COMT at concentrations of 50$\gamma$, 78$\gamma$ and 5 $\gamma$/cc, respectively.

EXAMPLE 2

A culture medium was prepared in a similar manner to Example 1 and a shaking culture was carried out in a similar manner. A plurality of 30 jar fermentors were prepared and into each of these jar fermentors 12 l of culture medium having a composition similar to Example 1 was introduced and sterilized at 120°C. for 30 minutes. After defoaming the thusly prepared culture medium by adding about 1.2 cc of silicone resin, 500 cc of culture liquid which had been cultured for 3 days was inoculated into each jar fermentor. While supplying sterilized air at a rate of 12 l/min. and agitating with an agitator operating at 250 rpm., the fermentation was conducted at 27°C. for 105 hours. During this process, silicone resin was added to the culture medium upon appearance of foams. Then, 45 l of culture liquid thusly prepared in four jar fermentors was filtered by a basket type centrifuge at a speed of 2500 rpm. to thereby obtain 40 l of filtrate and 5 kg. of fungus body solid portion (mycelium). When said solid mycelium was extracted with 5 l of methanol, 4.8 l of methanol solution was obtained. (Said filtrate, when diluted to a half concentration, presented 50% inhibition against COMT; whereas said methanol extract liquor, when diluted to a quarter concentration, presented 50% inhibition against COMT.) The methanol extract liquor was concentrated to 500 cc under diminished pressure and, after having been mixed with the filtrate, adjusted to pH 2.0 with 6 N HCl. The mixture was then extracted with butyl acetate at a ratio similar to Example 1. When the solvent layer was concentrated to dryness under diminished pressure, 80.0 g. of oily material was obtained. When this oily material was treated with 4.0 l of petroleum ether, 35.0 g. of brown powder was obtained from the petroleum ether-insoluble portion. This powder was found to have 85% of overall activity. This powder was column chromatographed in the same manner as Example 1 but this time, at a ratio three times as large as Example 1. As a result, 790 mg. of yellow powder, 250 mg. of yellow powder and 150 mg. of brown powder were obtained from the first, second and third active fractions, respectively. These powders were found to have 50% inhibition against COMT at a concentration of 20γ, 50γ and 2.0 γ/cc, respectively.

Furthermore, the first active fraction was dissolved in 10 cc methanol an chromatographed through a column charged with "Sephadex LH-20"(500 cc). It was observed that the fraction reached a peak at a level of 15 cc and was eluted concentrically at that level. After concentrating to dryness under diminished pressure, said active fraction was dissolved into 5 cc acetone. After adding 20 cc n-hexane, when this solution was allowed to stand overnight at room temperature, 18.5 mg. of light yellow needle crystal of compound (I) was obtained. The thusly obtained crystal was then recrystallized to obtain 15.0 mg. of pure 3',5,7-trihydroxy-4',6-dimethoxy-isoflavone (I).

In a similar manner, the second active fraction was chromatographed through a Sephadex LH-20 column to remove impurities. After adding 4 cc of benzene, the purified fraction was warmed to 60°C. for dissolving and allowed to stand overnight at room temperature. This gave 20 mg. of yellow crude crystal, which was then recrystallized to obtain 18.2 mg. of light yellow needle crystals of 3',5,7-trihydroxy-4',8-dimethoxy-isoflavone (II).

When the third active fraction dissolved in methanol was passed through a column charged with methanol and alumina (neutral alumina manufactured by Woelm) which is three times as much as the third fraction in weight, only the dyestuff was adsorbed on the alumina and colorless liquid was obtained. This liquid was then chromatographed through a column charged with Sephadex LH-20 and treated in a similar manner to the first fraction, to thereby obtain 11.5 mg. of colorless needle crystals of 3',7-dihydroxy-4',6,8-trimethoxy-isoflavone (III).

EXAMPLE 3

Actinomyces roseolus A.T.C.C. 31047 was cultured in a similar manner to Example 1 to obtain the primary strain, which was then cultured in a similar manner to Example 2 to obtain the secondary strain. A plurality of 200 l stainless steel tanks were prepared, into each of these tanks was introduced 120 l of culture medium prepared in a similar manner to Examples 1 and 2 and sterilized with steam for 30 minutes. After adding 0.01% of silicon resin, 5 l of secondary strain was inoculated in each tank and, while aerating with sterile air at a rate of 120 l/min. and agitating at 200 rpm, cultured at 27°C. for 96 hours.

The thusly prepared 240 l of culture liquid from two tanks was filtered with a filter press to obtain 200 l of filtrate and 40 kg. of mycelium (fungus body solid portion). The fungus solid body was extracted with 80 l of methanol to prepare 70 l of methanol extract liquid.

When diluted to three times as low a concentration, said filtrate presented a 50% inhibition; whereas said methanol extract liquid presented a 50% inhibition when diluted to six times as low a concentration. These filtrate and methanol extract liquids were purified by extraction at a ratio similar to Example 2 and crystallized to obtain 335 mg. of crystalline 3',5,7-trihydroxy-4',6-dimethoxy-isoflavone (I), 180 mg. of crystalline 3',5,7-trihydroxy-4',8-dimethoxy-isoflavone (II) and 78 mg. of crystalline 3',7-dihydroxy-4',6,8-trimethoxy-isoflavone (III).

We claim:
1. The process for the production of the compound having the formula

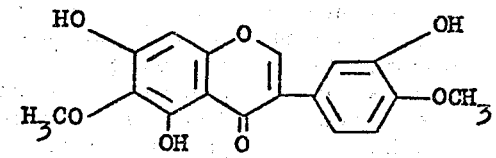

which comprises cultivating a strain of *Actinomyces roseolus* having the characteristics of strain A.T.C.C. 31047 at a temperature of about 25° to 35°C. for at least two days under submerged aerobic conditions in an aqueous assimilable carbohydrate solution containing an assimilable nitrogenous nutrient until a substantial amount of said compound is produced in said solution and then recovering said compound.

2. The process of claim 1 wherein the compound is recovered from the fermentation broth by solvent extraction at an acidic pH and then purified by chromatographic adsorption and elution.

3. The process for the production of the compound having the formula

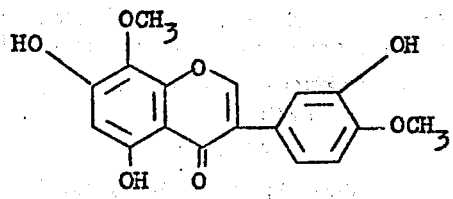

which comprises cultivating a strain of Actinomyces roseolus having the characteristics of strain A.T.C.C. 31047 at a temperature of about 25° to 35°C. for at least two days under submerged aerobic conditions in an aqueous assimilable carbohydrate solution containing an assimilable nitrogenous nutrient until a substantial amount of said compound is produced in said solution and then recovering said compound.

4. The process of claim 3 wherein the compound is recovered from the fermentation broth by solvent extraction at an acidic pH and then purified by chromatographic adsorption and elution.

5. The process for the production of the compound having the formula

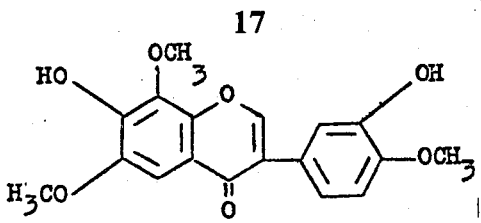

which comprises cultivating a strain of *Actinomyces roseolus* having the characteristics of strain A.T.C.C. 31047 at a temperature of about 25° to 35°C. for at least two days under submerged aerobic conditions in an aqueous assimilable carbohydrate solution containing an assimilable nitrogenous nutrient until a substantial amount of said compound is produced in said solution and then recovering said compound.

6. The process of claim 5 wherein the compound is recovered from the fermentation broth by solvent extraction at an acidic pH and then purified by chromatographic adsorption and elution.

* * * * *